US007409036B2

(12) United States Patent  
De Godzinsky et al.

(10) Patent No.: US 7,409,036 B2
(45) Date of Patent: Aug. 5, 2008

(54) METHOD AND ARRANGEMENT FOR IMPLEMENTING THE MOVEMENTS OF THE FUNCTIONAL ELEMENTS OF X-RAY IMAGING EQUIPMENT

(75) Inventors: Christian De Godzinsky, Vanda (FI); Timo Müller, Espoo (FI)

(73) Assignee: Planmeca Oy, Helsinki (FI)

( * ) Notice: Subject to any disclaimer, the term of this patent is extended or adjusted under 35 U.S.C. 154(b) by 40 days.

(21) Appl. No.: 10/472,944

(22) PCT Filed: Mar. 27, 2002

(86) PCT No.: PCT/FI02/00264

§ 371 (c)(1),
(2), (4) Date: Sep. 26, 2003

(87) PCT Pub. No.: WO02/076296

PCT Pub. Date: Oct. 3, 2002

(65) Prior Publication Data

US 2004/0076263 A1 Apr. 22, 2004

(30) Foreign Application Priority Data

Mar. 27, 2001 (FI) ................................. 20010634

(51) Int. Cl.
*A61B 6/14* (2006.01)
(52) U.S. Cl. .......................................... 378/39; 378/38
(58) Field of Classification Search ................... 378/38, 378/39, 40
See application file for complete search history.

(56) References Cited

U.S. PATENT DOCUMENTS

| 4,683,581 | A | | 7/1987 | Tammisalo et al. |
| 4,783,793 | A | | 11/1988 | Virta et al. |
| 5,387,856 | A | * | 2/1995 | Gilbert ...................... 318/807 |
| 5,425,065 | A | | 6/1995 | Järvenin |
| 5,511,106 | A | | 4/1996 | Doebert et al. |
| 6,028,412 | A | * | 2/2000 | Shine et al. .................. 318/696 |
| 6,091,216 | A | * | 7/2000 | Takahashi et al. ........... 318/254 |
| 6,208,107 | B1 | * | 3/2001 | Maske et al. ................ 318/685 |

OTHER PUBLICATIONS

Xu, Du et al., "A Method and Implementation of Fully Digitized Continuous Microstep for Step Motor," In: 1997 IEEE International Electric Machines and Drives Conference Records, 18-21 Mat 1997, pp. TC2/9.1-9.4.
International Search Report for PCT Application No. PCT/FI02/00264, issued by the Swedish Patent Office on Jul. 10, 2002.

* cited by examiner

*Primary Examiner*—Chih-Cheng G Kao
(74) *Attorney, Agent, or Firm*—Reed Smith LLP; Stanley P. Fisher, Esq.; Juan Carlos A. Marquez, Esq.

(57) ABSTRACT

The invention relates to a method and an arrangement for controlling the movements of the functional elements (13-16) of an X-ray apparatus, such as a panoramic X-ray apparatus. In the method, one or more power means (1) provided with a control system (21), a power stage (11) and a rotating power output shaft (2) is/are controlled so as to produce the aforesaid movements of the functional elements. The power output shaft (2) of the power means is caused to rotate by the control system and the power stage so that the power output shaft is in direct contact with the force receiving means (3, 3a) of the functional element.

23 Claims, 3 Drawing Sheets

Prior Art

METHOD AND ARRANGEMENT FOR IMPLEMENTING THE MOVEMENTS OF THE FUNCTIONAL ELEMENTS OF X-RAY IMAGING EQUIPMENT

FIELD OF THE INVENTION

The present invention relates to a method and an arrangement for implementing the movements of the functional elements of X-ray equipment, particularly panoramic X-ray equipment.

BACKGROUND OF THE INVENTION

Prior-art devices used in panoramic X-ray imaging for moving various functional elements, such as different supporting arms, an X-ray source and a film cassette or an image detector unit, include e.g. stepping motors. In this type of imaging, all movements of the functional elements have to be precise, accurate and smooth. An extremely critical movement is that of a light film cassette or image detector unit, which must be void of any vibrations as these would impair the imaging result. A serious problem associated with stepping motor drives is that, to achieve a sufficiently smooth and vibration-free motion, it has been necessary to use a gear solution of an extremely accurate and backlash-free design. The so-called zero-backlash type gear often used in this connection is because of its construction very expensive and requires adjustment and periodic maintenance, or replacing of it with new gears as a consequence of wear.

A prior-art panoramic X-ray apparatus is represented in U.S. Pat. No. 4,683,581 (FI patent no. 88671). The invention described in this publication mainly relates to the geometry of the movements of functional elements, and it proposes the use of stepping motors as a means of producing said movements. The specification presents no details as to how the stepping motor drive is to be implemented. In a commercial apparatus corresponding to this patent the functional elements are moved using stepping motors through gears.

Another prior-art panoramic X-ray apparatus that uses stepping motors is represented in U.S. Pat. No. 5,903,126 (FI patent 98011). This specification is mainly concerned with the control of stepping motors and the problems resulting from changes in the rotational speed of the motor. When the rotational speed of a stepping motor is changed, its control frequency changes in a notch-by-notch manner, and those momentary frequency changes are extensive at high rotational speeds of stepping motors. The solution according to this patent discloses a circuit arrangement by means of which the changes of speed can be performed in a stepless manner in the analog domain. However, this solution involves the drawback that, as the stepping motor works in a stepwise manner and at relatively high revolutions, it has to be operated in conjunction with a reduction gear, which is an expensive component requiring maintenance. Further drawbacks with this invention are the complexity of the circuit solution and the large number of components needed in it. Further, the number of components is multiplied when several stepping motors of the panoramic X-ray imaging apparatus are to be controlled.

A further common problem in the use of stepping motors has been the noise. Due to the solutions used to control and operate stepping motors, prior-art applications often produce an audible high-frequency whistling sound that does not naturally fit into a medical imaging situation and environment.

SUMMARY OF THE INVENTION

The object of the present invention is to reduce the above-mentioned drawbacks and to achieve an inexpensive method and arrangement for implementing the movements of the functional elements of X-ray imaging equipment, such as panoramic X-ray imaging apparatus, that will make it possible to obtain good imaging results. The method according to the invention is characterized by what is presented in the characterizing part of claim 1, and the arrangement according to the invention is characterized by what is presented in the characterizing part of claim 8. Other embodiments characteristic of the invention are presented in the other claims.

The solution according to the invention has the advantage that it makes it possible to achieve a vibration-free, smooth, precise and noiseless movement of functional elements, so that even in the case of a light functional element, such as a film cassette or image detector unit, that is prone to vibrations, a smooth motion throughout the travel of the element can be accomplished and thus also a good imaging result achieved. An additional advantage is that the number of components in the arrangement according to this solution is small, making it possible to achieve a low-cost solution for implementing the movements of the functional elements of a panoramic X-ray apparatus that is reliable in operation and as maintenance-free as possible. In addition, using the solution according to the invention, very accurate and short movements can be easily performed.

The solution according to the invention can be used in various applications in which a suitable power means, such as a stepping motor, is needed to produce an accurate, smooth and vibration-free movement at a desired speed in a correct direction. In particular, the invention is suited for use in a dental panoramic X-ray imaging apparatus, in which the advantages afforded by it will be effectively utilized.

BRIEF DESCRIPTION OF THE DRAWINGS

In the following, the invention will be described in detail by the aid of an example embodiment with reference to the attached drawings, wherein.

DETAILED DESCRIPTION OF THE INVENTION

Figure 1:
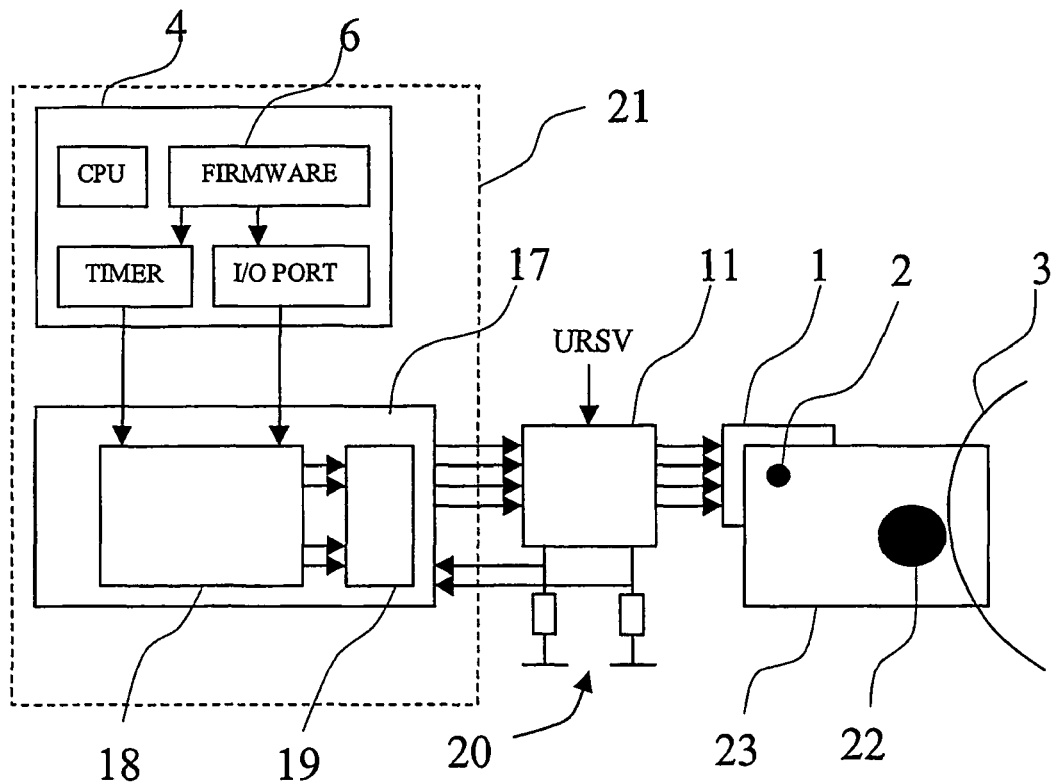
FIG. 1 presents simplified view of a prior-art solution.

FIG. 1 represents a prior-art solution for controlling the functional elements of a panoramic X-ray apparatus by means of a two-phase stepping motor 1. This figure presents a solution for the operation of only one motor. In this known solution, a two-phase stepping motor is controlled in current-mode using current measurement for feedback. The stepping motor can be driven in full-stepping mode and in micro-stepping mode and also in stepping modes between these. The control system 21 comprises a processor unit 4 and a fixed software package 6 called firmware, which contains unchanging physical constants and algorithms, among other things. In addition, the control system 21 comprises a traditional control circuit 17 for controlling a two-phase stepping motor, containing a motor-position-counter 18 and a chopper unit 19 comprising two current choppers. The position counter 18 comprises counters for full-step, half-step, quarter-step, and micro-step stepping modes, as well as two D/A converters for micro-stepping. Connected between the stepping motor 1 and the control system 21 is an output stage 11 and current measuring resistors 20 for two-channel current measurement. The output stage 11 contains at least two full H-bridges comprising 8 transistors, and preferably also an overheat protection system. The stepping motor 1 is controlled by means of four control voltages received from the output stage 11. In such a solution, the stepping motor shaft 2 has to be coupled to the functional element via an extremely accurate gear 23 that guarantees a sufficient torque as well as smooth and vibration-free operation, with a secondary shaft 22 transmitting the motion energy to a force receiving means 3 serving as a transmission means of the functional element. If the apparatus comprises more than one motor, then the number of components is increased correspondingly, except for the firmware. In particular, one such expensive gear is needed for each motor.

Figure 4:
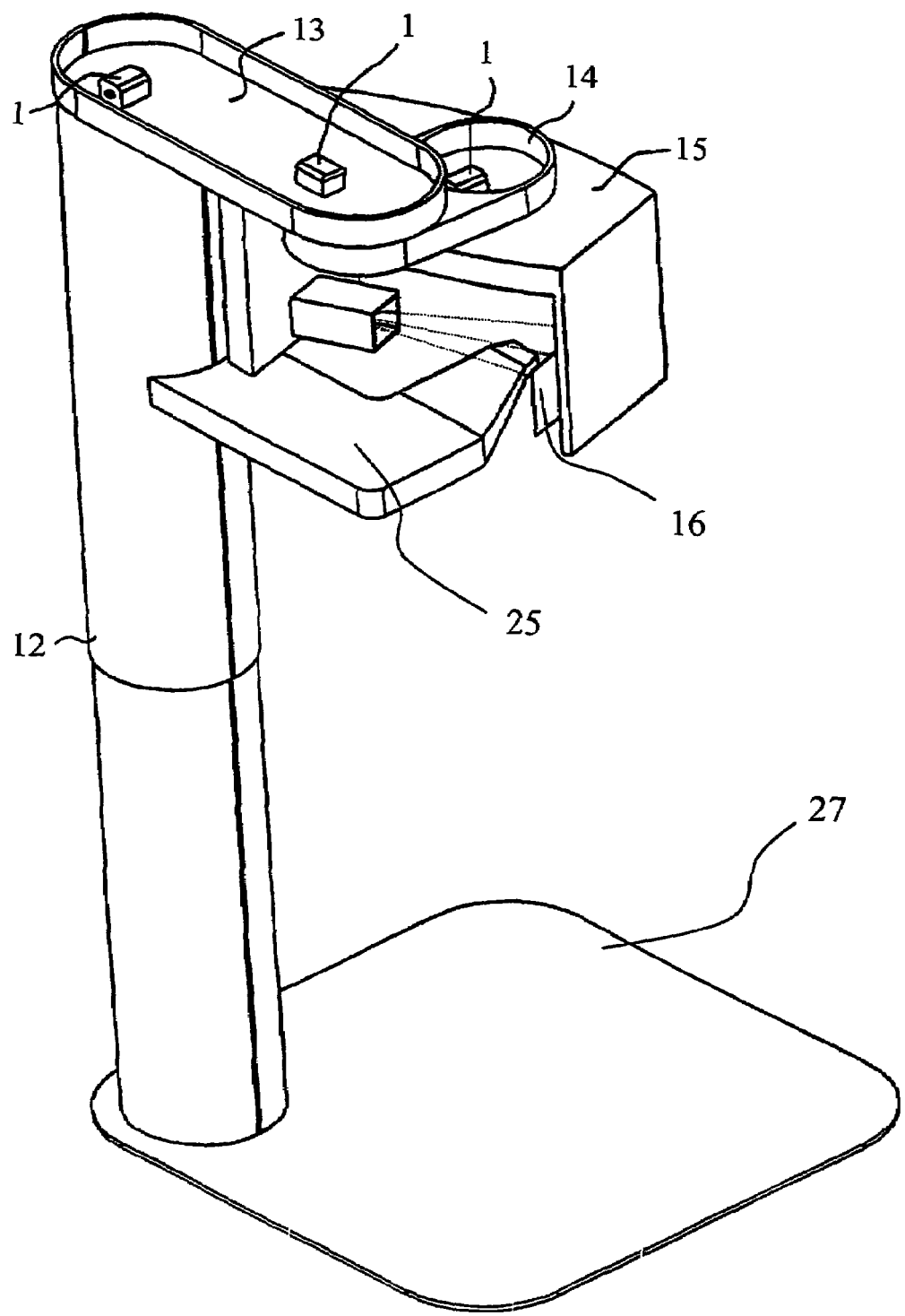
FIG. 4 presents a simplified and oblique top view of a typical panoramic X-ray apparatus, which can be provided with a solution according to the invention.

FIG. 4 presents a typical panoramic X-ray imaging apparatus. The apparatus comprises a base 27 and a column-like frame part 12 fixed by its lower end to the base, with a bracket-like supporting element 13 rotatably mounted on the upper end of the frame part 12 so that it can be turned relative to it, said supporting element 13 serving to support the imaging means. Correspondingly rotatably mounted on the outer end of the supporting element 13 is a bracket-like intermediate supporting element 14, on whose outer end is further rotatably mounted an imaging arm 15, or C-arm as it is called because of its shape, which supports the film cassette 16 and the X-ray source 24. The above-described elements 13-16 are commonly called "functional elements" of the panoramic X-ray apparatus. Moreover, attached to the column-like frame part 12 is a positioning support 25 for positioning the person to be imaged. Instead of on the column-like frame part, the swivellable supporting element 13 may as well be mounted on wall structures, and the other functional elements mentioned here may have a different structure and function. The structure illustrated in FIG. 4 has been simplified by omitting parts that are inessential to the invention. Besides, for the sake of clarity, the force receiving means 3 and 3a serving as transmission means of the functional elements 13-16 are not depicted in the figure. Likewise, the stepping motors 1 themselves are depicted in a simplified form, only indicating their placement.

According to the invention, the motion of the functional elements of the X-ray apparatus is preferably implemented by means of the control system 21 and a voltage-controlled power stage 11 used in it and by using a stepping motor specially designed for micro-stepping and of a size exceeding the normal size e.g. by one grade, in which case the stepping action of the stepping motor will be so fine, precise, smooth and vibration-free that a stepping motor 1 as mentioned above can be provided as a power means directly for each functional element without a need to use a separate gear 23 between the stepping motor and the force receiving means 3, 3a of the functional element. The shaft of the stepping motor may be provided with grooves, teeth or equivalent machined directly on the shaft, or it may be integrated with such as a friction wheel, toothed wheel or equivalent element that transmits the rotational motion of the shaft by rotating at substantially the same speed with the shaft. Hence, even the shaft itself may function as the friction wheel. In this context, the rotor shaft is called the power output shaft 2 of the stepping motor, regardless of whether it is a bare shaft or whether it comprises an integrated element transmitting the rotational motion as mentioned above. The output shaft 2 of the stepping motor can now be rotated slowly enough so that there is no need to use a transmission ratio reducing the number of revolutions to attenuate vibrations.

Figure 2:
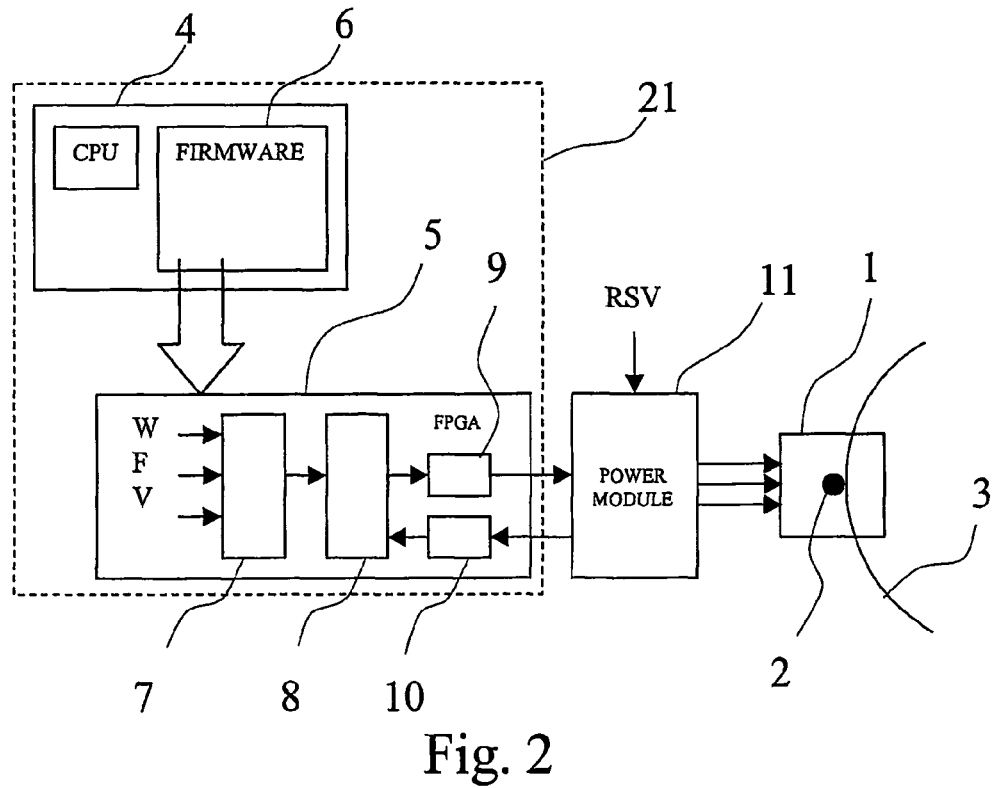
FIG. 2 presents a solution suited for use in the invention, depicted as in FIG. 1.

FIG. 2 presents a solution applicable to be used in the invention for controlling the stepping motor 1 and connecting it to a functional element. The control system 21 comprises a processor unit 4, which includes a firmware section 6 containing unchanging physical constants and algorithms, such as e.g. motor type, resonance and inductance data. In addition, the control system 21 comprises a logic unit 5, which receives data from the processor unit 4 and which may consist of e.g. a programmable logic circuit (FPGA) or ASIC circuit. The logic unit 5 contains a micro-stepping unit 7 operating with very small steps and receiving a basic waveform, frequency and voltage data (W, F and V) at its input, and a waveform synthesizer 8, which receives waveform, frequency and voltage parameters from the micro-stepping unit 7 and computes from these a new waveform to be input to the stepping motor 1. The logic unit further comprises a three-phase PWM generator 9, which receives a signal from the waveform synthesizer 8 and from which a digital signal is output to the power stage 11. FIG. 2 further shows a closed-loop motor protection circuit 10, which, however, does not take an actual functional part in the control of the motor. The protection circuit is designed to protect the motor against overcurrent and overheating. The power stage 11 comprises half-bridges for output voltages and it has a connection to the above-mentioned protection circuit 10. From the power stage 11, three synthesized, digital, fixed-frequency and pulse-width modulated square wave signals are taken to a three-phase stepping motor 1, which is specially designed for micro-stepping. A suitable fixed frequency is e.g. 40 kHz.

As a panoramic X-ray apparatus typically requires use of several stepping motors, all the other resources described above can be shared between all the motors, except for the power module 11 and the PWM generation logic 9, one of each being needed for each motor. As all the signals of the control system are digital and as it contains stored data regarding motor type, resistance, inductance and other properties required, a voltage can be fed into the motor without feedback. As the control system 21 knows the properties of the motor, the waveform synthesizer 8 will always produce correctly synthesized voltage signals, which make it possible to supply an appropriate current to the motor without feedback and associated problems, the possible only feedback 10 being provided to protect the motor.

Figure 5:
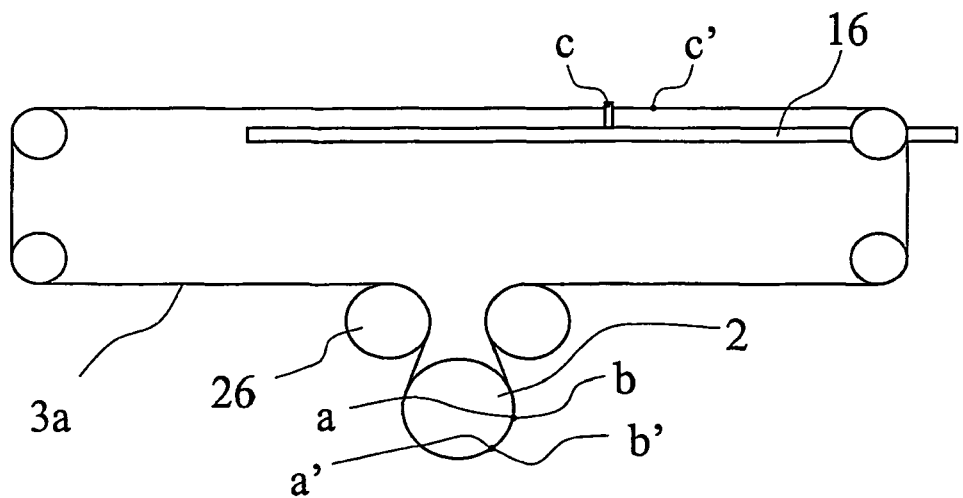
FIG. 5 presents a simplified top view of a film cassette actuating mechanism of a panoramic X-ray apparatus, provided with a solution according to the invention.

FIG. 5 presents a solution according to the invention for implementing the actuating mechanism of the film cassette 16 of a panoramic X-ray apparatus. The figure has been simplified by depicting only a skeleton diagram of the solution as seen from above the film cassette unit and with all superfluous components removed. The film cassette 16 is attached to a force receiving means 3a serving as a transmission means, consisting of e.g. an endless toothed belt, chain or equivalent. The transmission means 3a travels round the stepping motor shaft 2 while tightening means 26 placed near the shaft 2 press the transmission means 26 so that it is pressed against the shaft 2 with a desired force forming a loop around it and adapting to the substantially circular cross-sectional form of the shaft 2. The transmission means 3a forming an endless loop thus moves with the rotational motion of the shaft 2 either clockwise or counter-clockwise. The film cassette 16 is attached to the straight portion of the transmission means 3a and it moves with the movement of the transmission means 3a linearly either left or right e.g. along guide rails.

The movements of the functional elements 13-16 of the panoramic X-ray imaging apparatus can be controlled e.g. by using very slowly rotating three-phase stepping motors 1 as power means, by feeding each motor with three synthesized, digital, fixed-frequency and pulse-width modulated square wave signals without feedback. According to this method, the required technical data regarding the motors to be used, such as type, inductance and resistance, are fed beforehand into the control system 21 of the drive motors of the functional elements, and, based on these data, a synthesized sinusoidal voltage is supplied to the motors so that a desired current is achieved. From the control system firmware 6, digital signals containing the technical and other data necessary are supplied to the logic unit 5, where very fine micro-stepping of the stepping motors is generated on the basis of the signals fed into the logic unit, which include a basic waveform, frequency and voltage data W, F and V. From the micro-stepping unit 7, the signal data is taken as waveform, frequency and voltage parameters into the waveform synthesizer 8, where the final waveform to be supplied to the stepping motors is computed and from where a digital signal is further taken into a three-phase pulse-width-modulation generator 9, where the signal is subjected to pulse-width modulation. From the PWM generator 9, the digital pulse-width modulated signal is passed to a three-phase power module 11, from where three synthesized, digital, fixed-frequency and pulse-width modulated square wave signals are further supplied to the three-phase stepping motor 1, thus causing the stepping motor to rotate at the desired rotational speed. The rotor shaft of the stepping motor is further directly coupled to the force receiving means 3, 3a of the functional element, i.e. without a gear reducing the number of revolutions and increasing the torque, and the functional element is moved during the imaging at the desired speed in the desired direction by driving the motor with a number of revolutions that is higher than 0 but lower than 20, especially lower than 10 or lower than 5, preferably between 0.5-3 revolutions per second. In this situation, the velocity of the rotor of the stepping motor 1 and that of the functional element 13-16 actuated by it can be very close to each other.

A low rotational speed makes it possible to use a low transmission ratio, and consequently no reduction gear is needed. Thus, the ratio between the speed of movement of the stepping motor and that of the functional element actuated by it is very low, i.e. equal or higher than 1 but lower than 20, especially lower than 10 or lower than 5, preferably lower than 3.

Figure 3:
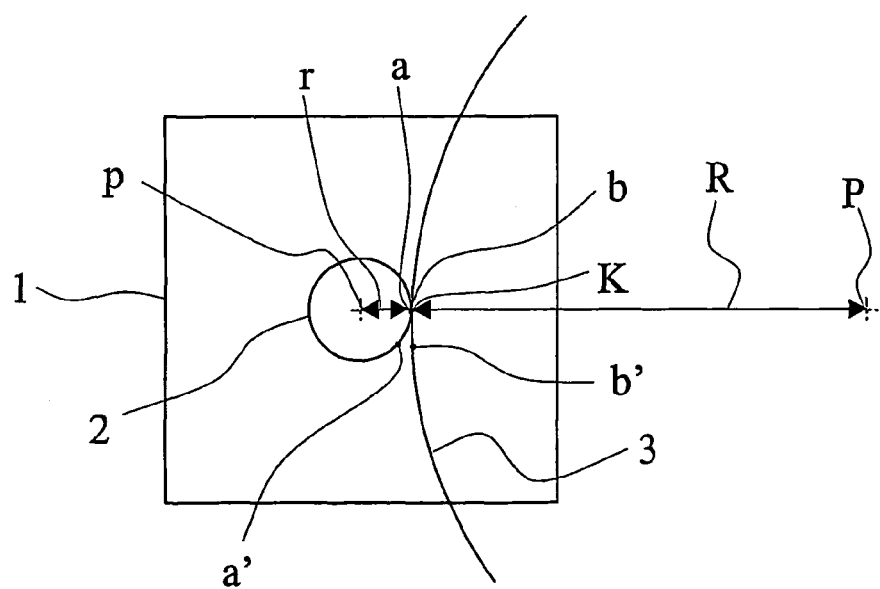
FIG. 3 presents a detail of a solution according to the invention at the point of contact between the shaft of a stepping motor and a force receiving means driven by it.

FIGS. 3 and 5 illustrate the synchronized motions and transmission ratios between the output shaft 2 of the stepping motor and the force receiving means 3, 3a of the functional elements. These relationships and ratios can be established e.g. by the aid of imaginary motion points a, a' on the circumferential contact surface of the output shaft 2, i.e. on that surface of the output shaft 2 which is in contact with the force receiving means 3, 3a of the functional element 13-16, and similarly imaginary motion points b, b' on the corresponding circumferential contact surface of the force receiving means 3, 3a. In connection with the force receiving means 3a of the film cassette, additional imaginary motion points c, c' are used as an aid. In this description, "circumferential contact surface" of the power output shaft 2 refers to that circumferential part of the rotor shaft of the stepping motor which is in contact with the force receiving means 3, 3a. If there is a power transmission element, such as a toothed wheel, integrated onto the rotor shaft, then the circumferential contact surface is the corresponding circumferential part of this element. The circumferential contact surface of the force receiving means 3, 3a is defined in a corresponding manner. The circumferential contact surface may also be an internal or external contact surface.

In the solution of the invention, when the output shaft 2 turns in a way that the motion point a on its circumferential contact surface moves a distance a-a', the force receiving means 3 of the functional element also turns so that motion point b on its circumferential contact surface moves a distance b-b', which is substantially equal to the distance of travel a-a' of motion point a. The same equality of traveling distances also applies in respect of the distances traveled by the output shaft 2 and the force receiving means 3a of the film cassette 16. As the film cassette 16 itself moves on a linear path, the equality of distances can be seen in that the distance c-c' traveled by the imaginary additional motion point c is substantially equal to distances a-a' and b-b'. Instead of equal distances traveled, one could also speak in terms of equal arcs a-a' and b-b' along the circumferential contact surface.

FIG. 3 illustrates the same from yet another viewpoint. Here, the point of contact between the power output shaft 2 of the stepping motor 1 and the force receiving means 3 is indicated as point K. The distance of the center of rotation p of the output shaft from the point of contact K is r. Similarly, the distance of the center of rotation P of the force receiving means from the point of contact K is R. In this type of embodiment of the invention, the rotational motion of the output shaft 2 of the stepping motor is transmitted directly to the force receiving means 3 of the functional element 13-15 so that the ratio of the rotational speed of the output shaft 2 to the rotational speed of the receiving means 3 is equal to the ratio of distance R to distance r. The same applies also when the film cassette 16 is being moved. In the case illustrated in FIG. 5, it is not possible to determine a single point of contact, but it can be seen that when the transmission ratio is unity, distances r and R are substantially equal and thus also the rotational speeds.

It is obvious to the person skilled in the art that the invention is not limited to the examples described above, but that it may be varied within the scope of the claims presented below. Thus, for example, the structure of the apparatus may differ from that described above in that, instead of stepping motors, servo or other corresponding motors may be used. Similarly, the structure of the transmission means may differ from that described above, they may be e.g. cogged belts, chains or equivalent. Moreover, the contact between the transmission means 3 and the shaft 2 may be either external or internal. The motion of the film cassette may also be implemented in a manner differing from the above-described solution using a belt or chain pressed into the form of a loop. A loop is not necessarily needed to achieve a reliable and backlash-free movement, but e.g. when an endless chain is used, it is sufficient to use a substantially straight chain with a suitable pressing force against a chain wheel mounted on the shaft 2. And e.g. as far as an embodiment according to FIG. 2 is concerned, it can also be constructed such that another than a three-phase PWM generator is used, and instead of fixed-frequency a variable frequency control is used.

The invention claimed is:

1. A dental panoramic X-ray apparatus, comprising:
   at least one arm, at least one of which includes an X-ray source and image detector unit of a dental panoramic X-ray apparatus;
   at least one power device having a rotating power output shaft; and
   a control device to control the power device, wherein the at least one arm is operatively connected to the power output shaft, the power device including a micro-stepping motor operatively connected to the power output shaft and configured to be controlled by the control device such that the power output shaft rotates in a micro-stepping mode, the power output shaft further configured to be operatively connected to the at least one arm, and to provide a ratio of a rotational speed of the power output shaft to a rotational speed of the at least one arm to be smaller than 20 and a continuous operating rotational speed of the power output shaft to be lower than 10 revolutions per second.

2. The dental panoramic X-ray apparatus according to claim 1, wherein the control device includes a circuit device to produce current for the power device using a digital signal.

3. The dental panoramic X-ray apparatus according to claim 1, wherein the control device is further configured to control the rotational speed of the power output shaft to be lower than 5 revolutions per second.

4. The dental panoramic X-ray apparatus according to claim 1, wherein the control device includes a processor unit containing a data storage unit in which technical values for the power device are stored, a logic unit connected to the processor unit and configured to produce digital control signals for the power output shaft to rotate in a stepwise manner, and an output stage configured to produce a voltage to generate a desired current for stepwise rotation control of the power device.

5. The dental panoramic X-ray apparatus according to claim 4, wherein the voltage is produced by the output stage digitally via pulse-width modulation.

6. The dental panoramic X-ray apparatus according to claim 4, wherein said logic unit contains a micro-stepping unit arranged to receive a basic waveform, frequency and voltage data (W, F and V) at an input thereof, and a waveform synthesizer configured to receive waveform, frequency and voltage parameters from the micro-stepping unit, and to compute a new waveform to be inputted to the at least one power device.

7. The dental panoramic X-ray apparatus according to claim 6, wherein the logic unit comprises a three-phase PWM generator, which is arranged to receive a signal from the waveform synthesizer and output a digital signal to a power stage.

8. The dental panoramic X-ray apparatus according to claim 1, further comprising:
a force receiving element operatively connected to transfer rotational movement from the power output shaft to the at least one arm, wherein a ratio of a speed of the power output shaft and a speed of the force receiving element is substantially the same as a ratio of a distance (R) between a point of contact (K) of the power output shaft with the force receiving element and a center (P) of the force receiving element to a distance (r) between a center (p) of the power output shaft and the point of contact (K) of the power output shaft.

9. The dental panoramic X-ray apparatus according to claim 1, wherein said at least one arm comprises means for receiving force generated by the at least one power device, the means for receiving force being arranged in direct contact with said power output shaft of the at least one power device.

10. The dental panoramic X-ray apparatus according to claim 1, wherein the control device contains stored data regarding type, resistance and inductance of the power device.

11. The dental panoramic X-ray apparatus according to claim 1, wherein the at least one power device is a at least three-phase stepping motor, and wherein the control device is arranged to feed the stepping motor with three synthesized, digital, fixed-frequency and pulse-width modulated square wave signals without feedback.

12. The dental panoramic X-ray apparatus according to claim 1, wherein the power output shaft is directly coupled to a force receiving means attached to the at least one arm.

13. A method for implementing movement of at least one arm of a panoramic X-ray apparatus having at least one arm, at least one of which carries an X-ray source and image detector unit of a dental panoramic X-ray apparatus, at least one power device having a rotating power output shaft and a control device to control the power device, wherein the at least one arm is operatively connected to the power output shaft, and the power device includes a micro-stepping motor operatively connected to the power output shaft, the method comprising the steps of:
controlling the micro-stepping motor so as to rotate the power output shaft in a micro-stepping mode;
controlling a continuous operating rotational speed of the power output shaft such that a ratio of a rotational speed of the power output shaft to a rotational speed of the at least one arm is smaller than 20; and
controlling the rotational speed of the power output shaft to be lower than 10 revolutions per second.

14. The method according to claim 13, wherein the step of controlling the micro-stepping motor includes digitally generating a current for the power device so as to actuate the at least one arm.

15. The method according to claim 13, further comprising the step of:
controlling the rotational speed of the power output shaft to be lower than 5 revolutions per second.

16. The method according to claim 13, further comprising the step of:
storing known technical values of the power device in the control device; and
processing control signals in digital form based on the stored values so as to control rotation of the power output shaft in steps.

17. The method according to claim 13, further comprising the step of:
storing known properties of the power device in the control device; and
generating digital control pulses so as to produce a current for controlling the power device.

18. The method according to claim 17, wherein the current is produced via pulse-width modulation.

19. The method according to claim 13, further comprising the step of:
controlling the rotational speed of the power output shaft to be lower than 3 revolutions per second.

20. The method according to claim 13, further comprising the steps of:
inputting data regarding a type, inductance and resistance of the power device to be used into the control device; and
based on the inputted data, supplying a synthesized sinusoidal voltage to the power device so that a desired current is achieved.

21. The method according to claim 13, further comprising the step of:
supplying digital signals containing technical data of the power device from a control system firmware to a logic unit, where very fine micro-stepping of the micro-stepping motor is generated on the basis of the signals fed into a micro-stepping unit of the logic unit, which include a basic waveform, frequency and voltage data (W, F and V), taking the signal data from the micro-stepping unit as waveform, frequency and voltage parameters into a waveform synthesizer, where the final waveform to be supplied to the power device is computed and from where a digital signal is further taken into a three-phase pulse-width-modulation generator, where the digital signal is subjected to pulse-width modulation, and further, from the PWM generator, the digital pulse-width modulated signal is passed to a three-phase power module, from where three synthesized, digital, fixed-frequency and pulse-width modulated square wave signals are supplied to the power device arranged to be a three-phase stepping motor, thus causing the stepping motor to rotate at the desired rotational speed.

22. The method according to claim 13, further comprising the step of arranging a power receiving means arranged to the at least one arm in direct contact with said power output shaft of the micro-stepping motor.

23. The method according to claim 13, wherein the power output shaft is directly coupled to a force receiving means attached to the at least one arm.

* * * * *